US006313330B1

(12) United States Patent
Kiyohara et al.

(10) Patent No.: US 6,313,330 B1
(45) Date of Patent: Nov. 6, 2001

(54) PROCESSES OF SELECTIVELY SEPARATING AND PURIFYING EICOSAPENTAENOIC AND DOCOSHEXAENOIC ACIDS OR THEIR ESTERS

(75) Inventors: Satoshi Kiyohara; Shiro Fujita, both of Saitama-ken (JP)

(73) Assignee: Nisshin Pharma Inc., Tokyo (JP)

( * ) Notice: Subject to any disclaimer, the term of this patent is extended or adjusted under 35 U.S.C. 154(b) by 0 days.

(21) Appl. No.: 09/604,766

(22) Filed: Jun. 28, 2000

(30) Foreign Application Priority Data

Jun. 28, 1999 (JP) .................................................. 11-181407

(51) Int. Cl.⁷ ..................................................... C07C 51/43
(52) U.S. Cl. ............................................. 554/193; 554/191
(58) Field of Search ...................................... 554/191, 193

Primary Examiner—Deborah D. Carr

(57) ABSTRACT

A process of selectively separating and purifying eicosapentaenoic and docosahexaenoic acids or the esters thereof from a mixture comprising a highly unsaturated fatty acid or the derivative thereof, which comprises the steps of:

flowing an aqueous medium comprising a silver salt through a column filled with a diatomaceous earth to carry the silver salt on the diatomaceous earth;

flowing a solvent solution of a mixture comprising the highly unsaturated fatty acid or the derivative thereof through the silver salt-carried diatomaceous earth in the column; and flowing a developing solvent through the column.

5 Claims, No Drawings

PROCESSES OF SELECTIVELY SEPARATING AND PURIFYING EICOSAPENTAENOIC AND DOCOSHEXAENOIC ACIDS OR THEIR ESTERS

FIELD OF THE INVENTION

This invention relates to a process of selectively separating and purifying eicosapentaenoic and docosahexaenoic acids or the esters thereof from a mixture comprising a highly unsaturated fatty acid or the derivative thereof.

BACKGROUND OF THE INVENTION

There are known highly unsaturated fatty acids or the derivatives thereof such as the esters thereof which originate from fish oils such as oils of sardines, mackerels, tunas or the like. Especially, eicosapentaenoic acid (EPA) and docosahexaenoic acid (DHA) and the esters thereof have been used in the field of health foods and drugs because of their pharmacological effects.

The known processes for the purification of these unsaturated fatty acids or the derivatives thereof are a urea-addition process, a precision distillation process, a chromatographic process, a supercritical fluid extraction process and the like. However, these prior processes are individually difficult to purify a mixture comprising highly unsaturated fatty acids or their derivatives originating from fish oils, in high purity, without modification, in large quantity and at low cost. In the urea-addition process, the resultant mixture comprising highly unsaturated fatty acids or their esters is low in a degree of purity. In the precision distillation process, polymerization and isomerization occur with easy modification of the product and it is difficult to remove eicosatetraenoic acid (ETA) or its ester which is not desirable when used as drugs and foods. Further, the chromatographic and supercritical fluid extraction processes are not suitable for the separation and purification on an industrial scale.

Japanese Patent Kokai 9-151390 discloses a process for the purification of a highly unsaturated fatty acid and the derivative thereof, which comprises contacting a mixture of highly unsaturated fatty acids or their derivatives with a carrier carrying a silver salt, and subsequently separating and extracting by contacting the carrier with a solvent. It is described therein that silica gel, zeolite, kaolin, active china clay, pearlite and the combination thereof are used as a carrier. However, this publication gives no reference to the use of diatomaceous earth and the effect achieved thereby. Further, this prior process gives the limitations that the amount of the carrier for the silver salt should be 19 parts by weight in terms of silver relative to 45–55 parts by weight of the carrier, and further, that the amount of the mixture of highly unsaturated fatty acids or their derivatives to be contacted with the silver salt-carried carrier should be 15 parts by weight. The departure from such limitations results in lowering a degree of purification. Although the prior process can separate and purify a highly unsaturated fatty acid component in high purity, there are several problems that a process for preparing the silver-carried carrier is complicated, and that an extraction operation including repeated stirring and filtering is troublesome.

There has been a demand for a practical process of selectively separating and purifying desired EPA and DHA from fish oils containing various highly unsaturated fatty acids and their derivatives.

SUMMARY OF THE INVENTION

An object of the invention is to provide a process of separating and purifying EPA and DHA in high purity, which has more increased weight ratio of a silver salt to a carrier than the prior art process, thus exhibiting a high processing power, and which eliminates the incorporation of a silver compound.

The object of the invention can be attained by using a diatomaceous earth as a carrier for carrying a silver salt, filling the carrier in a column, flowing an aqueous medium containing the silver salt through the column to easily prepare a silver-carried carrier, and flowing a specified developing solvent in turn through the column.

The present invention provides a process of selectively separating and purifying eicosapentaenoic and docosahexaenoic acids or the esters thereof from a mixture comprising a highly unsaturated fatty acid or the derivative thereof, which comprises the steps of: flowing an aqueous medium comprising a silver salt through a column filled with a diatomaceous earth to carry the silver salt on the diatomaceous earth;

flowing a solvent solution of a mixture comprising the highly unsaturated fatty acid or the derivative thereof through the silver salt-carried diatomaceous earth in the column; and flowing a developing solvent through the column.

The present invention of the above construction can effectively separate and purify EPA and DHA from the mixture comprising highly unsaturated fatty acids or the derivatives thereof originating from fish oils, and further, it can inhibit an effusion of a silver, thus preventing the reduction in separation ability and the incorporation of silver into a separated and purified product. Moreover, the present process can reduce the content of eicosatetraenoic acid ($\omega$6 ETA) which is not desirable in health foods and drugs, as low as possible.

DETAILED DESCRIPTION OF THE INVENTION

The raw materials, a mixture comprising highly unsaturated fatty acids or their derivatives which are used for purification in the present invention can include, but are not limited to, those originating from fish oils such as oils of sardines, mackerels, tunas or the like, which contain highly unsaturated fatty acids, e.g., ETA, EPA or DHA, ester derivatives of these unsaturated fatty acids or the mixtures thereof. The composition of the raw materials may be variable when they originate from fish oils. Thus the degree of separation or purification of EPA and DHA or their esters may vary depending on the composition of the raw material. Even if several % or more of ETA is contained in the raw material, the present process can selectively separate and purify EPA and DHA, and further, reduce the content of ETA to a specified low level.

The present invention is characterized by using the diatomaceous earth as the carrier for carrying the silver salt. The diatomaceous earth is a fossil of a single cell plant which is a kind of the waterweed propagating in both areas of the fresh water and the vexation water. One of the reasons for the selective use of diatomaceous earth is that the ability to hold water in the diatomaceous earth is about two times as high as that in other materials when the silver salt is carried on the diatomaceous earth in the form of a solution dissolved in the aqueous medium. For reference, the ability to hold water is compared below, using a pore volume per weight (oil absorption, ml/g).

| Silica gel | Zeolite | Kaolin | Active china clay | Pearlite | Diatomaceous earth |
|---|---|---|---|---|---|
| 0.75 | 0.45 | 0.5–0.55 | 0.55 | — | 1≧ |

The diatomaceous earth can be usually used in its uncalcined or calcined form, but the calcined earth is preferable. The calcined diatomaceous earth can be produced by crushing a raw diatomaceous earth, drying the crushed product, subjecting it to repeated grinding and classification operations to remove impurities, calcining the classified product at high temperature, and further subjecting it to repeated grinding and classification operations to adjust the particle size. It is preferable that the diatomaceous earth has a pore size of 0.1–10 $\mu$m, a specific surface area of 0.5–50 $m^2/g$ and a pore volume of 1–10 ml/g for increasing the ability to hold an aqueous silver salt solution and securing good contact with highly unsaturated fatty acids or their derivatives to be treated. It is more preferable that the diatomaceous earth has a bulk density of 0.1–0.3 g/ml, taking the size of column into consideration. The diatomaceous earth which can be used in the present invention is commercially available, but not limited to a specified one, a typical example of which is "Extrelut® 13076" available from Merck Co., Ltd.

As the silver salts to be carried on the diatomaceous earth, any silver salts can be used if they can form a complex on the diatomaceous earth with the mixture comprising highly unsaturated fatty acids or their derivatives. Silver nitrate is most preferably used, taking into consideration its easy handling and availability as well as its easy recovery and reuse.

It is desirable that the amount of the silver salts carried on the diatomaceous earth is not more than 65% by weight in terms of silver, preferably from more than 55% by weight to not more than 65% by weight, based on the weight of the diatomaceous earth, taking into consideration the downsizing of column and the high operation capability.

In general, as the amount of the silver salts carried on a prescribed amount of the diatomaceous earth increases, the amount of the raw material treated, i.e., the amount of the mixture comprising highly unsaturated fatty acids or their derivatives treated can be increased. From such viewpoint, the amount of the silver salt carried in the present invention can be increased to 65% by weight at maximum, which results in an advantage that the amount of the raw materials treated can be increased largely.

As a method of carrying a silver salt on a carrier, Japanese Patent Kokai 9-151390 discloses a method of immersing the carrier in an aqueous solution of the silver salt, followed by drying. However, this method is difficult to control water content. In contrast, the present invention has an advantage that carrying of the silver salt on the diatomaceous earth can be easily done by simply flowing the aqueous medium containing the silver salt (e.g., 50% aqueous solution of the silver salt) through the diatomaceous earth which is dry-filled in the column, e.g., filled in substantially the same weight as the silver salt. The aqueous medium for the silver salt used is water, methanol, acetone or the like, but water is preferable.

According to the process of the present invention, the column filled with the silver-carried diatomaceous earth can be prepared by filling the diatomaceous earth in the column and flowing the aqueous medium containing the silver salt through the column to carry the silver salt on the diatomaceous earth. Then a solvent solution of the mixture comprising highly unsaturated fatty acids or their derivatives to be separated and purified is contacted with the diatomaceous earth to form a complex with the silver salt (silver ion). Subsequently, the column is developed with a small quantity of a specific solvent to selectively separate and purify EPA, DHA or their esters. A representative example of the solvent solution of the said mixture is the hexane solution, but not limited thereto. The solvents used for the preparation of the said solution may be identical with the developing solvents.

In the present invention, a column can be used several times, and the solvent solution of the mixture comprising highly unsaturated fatty acids or their derivatives to be separated and purified may be contacted with the diatomaceous earth after the column filled with the silver-carried diatomaceous earth has been previously displaced with hexane.

As the developing solvents which can be used in the present invention for the separation and purification of the desired product, any solvents can be used if they can exhibit high selectivity and extraction ability with a small quantity of solvent and can inhibit a leakage of the silver salt, but pentane, hexane, heptane, toluene, xylene, methanol, isopropyl alcohol, ethyl acetate or the mixture thereof are especially preferable. The type and amount of the solvents used can be decided suitably so as to provide optimum conditions.

With regard to the selectivity of extraction, the extracts having different compositions can be obtained by operating the polarity of the developing solvent. In the most preferred embodiments of the present invention, an elution may be carried out by using hexane initially and then toluene containing 0.5% by volume of methanol as the developing solvent.

In the present invention, the extraction is performed at an ambient temperature, preferably at a temperature of 0° C. to 30° C. This can provide a stabilized extract with less possibility of an alteration by a thermal isomerization or the like. An atmosphere upon extraction is preferably replaced with an inert gas such as nitrogen, argon or the like to prevent the mixture comprising highly unsaturated fatty acids or their esters from the influence such as oxidation or the like.

In the present invention, the pore volume of the diatomaceous earth is 1–10 ml/g, which indicates that the amount of the aqueous medium held per gram of the diatomaceous earth is 1–10 ml. For instance, when silver is carried in the form of an aqueous silver nitrate solution, silver nitrate forms its saturated solution with water of about half amount based on the weight of silver nitrate. Accordingly, only 50% of the pore volume of the diatomaceous earth is used even if silver nitrate of the same weight as the diatomaceous earth is held in the form of the aqueous solution. This can inhibit an effusion of silver. That is, two-fold amounts of the diatomaceous earth based on the aqueous medium in the aqueous silver nitrate solution can be used, which results in no effusion of the silver salt from the column when the extraction is carried out with an organic solvent such as hexane or the like.

The invention is further illustrated by the following Examples and Comparative Examples.

EXAMPLE 1

A glass column (20 mm in inside diameter×300 mm in length) was dry-filled with 20 g of diatomaceous earth ("Extrelut® 13076" available from Merck Co., Ltd.) having a pore size of 4000 nm, a specific surface area of 1.01 m²/g, a pore volume of 1.2 ml/g and a bulk density of 0.24 g/ml. An aqueous solution of 20 g of silver nitrate in 10 ml of water was flowed through the column filled with the diatomaceous earth. The column was allowed to stand for 30 minutes to carry the silver salt on the diatomaceous earth. Subsequently, hexane was flowed through the column to displace the column with hexane.

10 g of a raw material, an ethyl ester mixture of a highly unsaturated fatty acid having the composition shown in Table 1 were dissolved in 10 ml of hexane to prepare a hexane solution. This solution was flowed through the column. Initially, the column was developed by 90 ml of hexane at a linear velocity of 0.5 to 5.0 cm/min, an eluate from the column was collected, and the solvent was removed under reduced pressure to concentrate the eluate, thus giving 5.76 g (yield 57.6%) of the first effluent fraction. Next, the column was developed by 290 ml of a toluene mixed solvent containing 0.5% by volume of methanol at a linear velocity of 0.5 to 5.0 cm/min, an eluate from the column was collected, and the solvent was removed under reduced pressure to concentrate the eluate, thus giving 3.62 g (yield 36.2%) of the second effluent fraction.

Further, the column was developed by 100 ml of a toluene mixed solvent containing 0.5% by volume of methanol at a linear velocity of 0.5 to 5.0 cm/min, an eluate from the column was collected, the solvent was removed under reduced pressure to concentrate the eluate, thus giving 0.65 g (yield 6.5%) of the third effluent fraction. The resultant purified ethyl esters of fatty acids were analyzed by gas chromatography, with the following results shown in Table 1.

The gas chromatography used in the analysis was Model 263-560 manufactured by Hitachi Co., Ltd. The column conditions are shown below.
Packed column: Silar-10C Uniport, HP 80/100, 3 mm I.D.×2 m
Detector: FID
Column temperature: 200° C.
Inlet temperature: 250° C.
Detector temperature: 250° C.
Carrier gas: nitrogen
Flow rate: adjusted so as to provide about 20 minutes of a retention time of EPA

TABLE 1

| | Content of ethyl ester of each fatty acid (%) | | | | |
|---|---|---|---|---|---|
| | ETA (ω6) | ETA (ω3) | EPA | DHA | Others |
| Composition of raw material before purification | 3.65 | 2.07 | 45.02 | 8.73 | 40.53 |
| First effluent fraction | 6.61 | 3.83 | 19.22 | 0.05 | 70.29 |
| Second effluent fraction | 0.33 | 0.12 | 91.58 | 0.95 | 7.02 |
| Third effluent fraction | 0.58 | 0.29 | 32.48 | 65.34 | 1.31 |

The above result clearly shows that ETA (ω6, ω3) contained in the raw material before purification was largely reduced. Further, it is evident that the ethyl esters of EPA and DHA were selectively purified.

EXAMPLE 2

A glass column (20 mm in inside diameter×300 mm in length) was dry-filled with 20 g of diatomaceous earth ("Extrelut® 13076" available from Merck Co., Ltd.) having a pore size of 4000 nm, a specific surface area of 1.01 m²/g, a pore volume of 1.2 ml/g and a bulk density of 0.24 g/ml. An aqueous solution of 20 g of silver nitrate in 10 ml of water was flowed through the column filled with the diatomaceous earth. The column was allowed to stand for 30 minutes to carry the silver salt on the diatomaceous earth. Subsequently, hexane was flowed through the column to displace the column with hexane.

10 g of a raw material, an ethyl ester mixture of a highly unsaturated fatty acid having the composition shown in Table 2 were dissolved in 10 ml of hexane to prepare a hexane solution. This solution was flowed through the column. Initially, the column was developed by 90 ml of hexane at a linear velocity of 0.5 to 5.0 cm/min, an eluate from the column was collected, and the solvent was removed under reduced pressure to concentrate the eluate, thus giving 6.76 g (yield 67.6%) of the first effluent fraction. Next, the column was developed by 290 ml of a toluene mixed solvent containing 0.5% by volume of methanol at a linear velocity of 0.5 to 5.0 cm/min, an eluate from the column was collected, and the solvent was removed under reduced pressure to concentrate the eluate, thus giving 2.96 g (yield 29.6%) of the second effluent fraction.

The resultant purified ethyl esters of fatty acids were analyzed by gas chromatography, with the following results shown in Table 2.

TABLE 2

| | Content of ethyl ester of each fatty acid (%) | | | | |
|---|---|---|---|---|---|
| | ETA (ω6) | ETA (ω3) | EPA | DHA | Others |
| Composition of raw material before purification | 3.53 | 1.35 | 93.44 | 0.25 | 1.43 |
| First effluent fraction | 5.14 | 1.95 | 90.72 | 0.02 | 2.17 |
| Second effluent fraction | 0.19 | 0.09 | 98.70 | 0.47 | 0.55 |

The above result clearly shows that even if the raw material contained EPA of high purity, ETA (ω6, ω3) contained therein before purification was largely reduced. Further, it is evident that the ethyl ester of EPA was selectively purified in a degree of 98% or more, which satisfies a level for drug.

EXAMPLE 3 and Comparative Example 1 i) For Example 3, three glass columns (20 mm in inside diameter×300 mm in length) were each dry-filled with 20 g of diatomaceous earth ("Extrelut® 13076", available from Merck Co., Ltd.) having a pore size of 4000 nm, a specific surface area of 1.01 m²/g, a pore volume of 1.2 ml/g and a bulk density of 0.24 g/ml. Then 14.20 g, 17.31 g and 20.42 g of silver nitrate were dissolved in 7.1 ml, 8.7 ml and 10.2 ml of water, respectively to prepare aqueous solutions of silver nitrate. Each aqueous solution of silver nitrate was flowed through each column filled with the diatomaceous earth. The columns were allowed to stand for 30 minutes to carry the silver salt on the diatomaceous earth. In this case, silver nitrate carried on the diatomaceous earth in each column was 45%, 55% and 65%, respectively in terms of silver based on the weight of the diatomaceous earth. Subsequently, hexane was flowed through the column to displace the column with hexane.

ii) For Comparative Example 1, three glass columns (20 mm in inside diameter×300 mm in length) were each dry-filled with 20 g of silica gel ("Silica gel® 60 107734", available from Merck Co., Ltd.) having a particle size of 0.063–0.2 mm. Then 14.20 g, 17.31 g and 20.42 g of silver nitrate were dissolved in 7.1 ml, 8.7 ml and 10.2 ml of water, respectively to prepare aqueous solutions of silver nitrate. Each aqueous solution of silver nitrate was flowed through each column filled with silica gel. The columns were allowed to stand for 30 minutes to carry the silver salt on silica gel. In this case, silver nitrate carried on silica gel in each column was 45%, 55% and 65%, respectively in terms of silver based on the weight of the silica gel. Subsequently, hexane was flowed through the column to displace the column with hexane.

iii) 7.1 g, 8.7 g and 10.2 g of a raw material, an ethyl ester mixture of a highly unsaturated fatty acid having the composition shown in Table 1 were dissolved in 7.1 ml, 8.7 ml and 10.2 ml of hexane, respectively to prepare hexane solutions. Each hexane solution was flowed through each column. Initially, the columns were developed by 63.9 ml, 78.3 ml and 91.8 ml of hexane, respectively at a linear velocity of 0.5 to 5.0 cm/min, an eluate from the column was collected, and the solvent was removed under reduced pressure to concentrate the eluate, thus giving the first effluent fractions. Next, the columns were developed by 206 ml, 252 ml and 296 ml of a toluene mixed solvent containing 0.5% by volume of methanol, respectively at a linear velocity of 0.5 to 5.0 cm/min, an eluate from the column was collected, and the solvent was removed under reduced pressure to concentrate the eluate, thus giving the second effluent fractions. Further, the columns were developed by 71 ml, 87 ml and 102 ml of a toluene mixed solvent containing 0.5% by volume of methanol, respectively at a linear velocity of 0.5 to 5.0 cm/min, an eluate from the column was collected, and the solvent was removed under reduced pressure to concentrate the eluate, thus giving the third effluent fractions.

The purified ethyl esters of fatty acids obtained in the second effluent fractions were analyzed by gas chromatography, with the following results shown in Table 3.

was observed in the effluent from the diatomaceous earth-filled column. In the case of silica gel, the amount of silver salt carried beyond 45% in terms of silver, based on the weight of the carrier, was beyond the limits of the ability of silica gel to hold the silver salt thereon, by which it was confirmed that the silver salt effused from the column. From this result, it was presumed that the prior process using silica gel as the carrier would require an additional step for the separation of silver, since a silver ion would be incorporated in the effluent after the purification by column, and that the separation ability of the column was reduced due to a reduced amount of silver ion within the column.

EXAMPLE 4

A glass column (90 mm in inside diameter×300 mm in length) was dry-filled with 500 g of diatomaceous earth ("Extrelut® 13076"available from Merck Co., Ltd.) having a pore size of 4000 nm, a specific surface area of 1.01 $m^2$/g, a pore volume of 1.2 ml/g and a bulk density of 0.24 g/ml. An aqueous solution of 500 g of silver nitrate in 250 ml of water was flowed through the column filled with the diatomaceous earth. The column was allowed to stand for 30 minutes to carry the silver salt on the diatomaceous earth. Subsequently, hexane was flowed through the column to displace the column with hexane.

250 g of a raw material, an ethyl ester mixture of a highly unsaturated fatty acid having the composition shown in Table 4 were dissolved in 250 ml of hexane to prepare a hexane solution. This solution was flowed through the column. Initially, the column was developed by 2250 ml of hexane at a linear velocity of 0.5 to 5.0 cm/min, an eluate from the column was collected, and the solvent was removed under reduced pressure to concentrate the eluate, thus giving 157.18 g (yield 62.87%) of the first effluent fraction. Next, the column was developed by 7250 ml of a toluene mixed solvent containing 0.5% by volume of methanol at a linear velocity of 0.5 to 5.0 cm/min, an eluate from the column was collected, and the solvent was removed under reduced pressure to concentrate the eluate, thus giving 84.93 g (yield 33.97%) of the second effluent fraction.

Further, the column was developed by 2500 ml of a toluene mixed solvent containing 0.5% by volume of metha-

TABLE 3

| | Silver nitrate (g) | Silver salt carried (%) | Raw material mixture (g) | Content of ethyl ester of each fatty acid (%) | | | | | Yield of second effluent fraction (%) | Effluence of silver |
|---|---|---|---|---|---|---|---|---|---|---|
| | | | | ETA (ω6) | ETA (ω3) | EPA | DHA | Others | | |
| Example 3 | 14.20 | 45 | 7.1 | 0.16 | 0.29 | 85.92 | 5.52 | 8.11 | 34.9 | Not detected |
| | 17.31 | 55 | 8.7 | 0.04 | 0.08 | 86.55 | 6.61 | 6.72 | 36.8 | Not detected |
| | 20.46 | 65 | 10.2 | 0.08 | 0.13 | 85.17 | 7.20 | 7.42 | 32.8 | Not detected |
| Comparative Example 1 | 14.20 | 45 | 7.1 | 0.16 | 0.25 | 88.93 | 2.30 | 8.36 | 31.8 | Detected |
| | 17.31 | 55 | 8.7 | 0.28 | 0.36 | 89.36 | 2.42 | 7.58 | 25.3 | Detected |
| | 20.46 | 65 | 10.2 | 0.15 | 0.17 | 90.86 | 1.86 | 6.96 | 26.2 | Detected |

As shown in Table 3, even if the amount of silver salt carried was varied, the diatomaceous earth as a carrier exhibited the slightly higher ability of separating ETA (ω6, ω3) than the silica gel. When a saturated sodium chloride solution was added to the effluent, the effluent from the silica gel-filled column became clouded, by which it was confirmed that silver chloride formed. However, no alteration nol at a linear velocity of 0.5 to 5.0 cm/min, an eluate from the column was collected, and the solvent was removed under reduced pressure to concentrate the eluate, thus giving 2.59 g (yield 1.04%) of the third effluent fraction. The resultant purified ethyl esters of fatty acids were analyzed by gas chromatography, with the following results shown in Table 4.

TABLE 4

| | Content of ethyl ester of each fatty acid (%) | | | | |
|---|---|---|---|---|---|
| | ETA (ω6) | ETA (ω3) | EPA | DHA | Others |
| Composition of raw material before purification | 2.33 | 2.03 | 42.62 | 7.69 | 45.33 |
| First effluent fraction | 3.61 | 3.24 | 22.64 | 0.0 | 70.51 |
| Second effluent fraction | 0.08 | 0.02 | 92.39 | 2.65 | 4.86 |
| Third effluent fraction | 0.35 | 0.0 | 3.88 | 92.17 | 3.60 |

Even if the size of the column was increased, the present process exhibited high selectivity of EPA and DHA, as in Example 1, and provided the reproducibility of Example 1 in respect of the load of column, amount of developing solvents and yield of the resultant purified fatty acids.

EXAMPLE 5

A glass column (60 mm in inside diameter×495 mm in length) was dry-filled with 400 g of diatomaceous earth ("Extrelut® 13076" available from Merck Co., Ltd.) having a pore size of 4000 nm, a specific surface area of 1.01 m²/g, a pore volume of 1.2 ml/g and a bulk density of 0.24 g/ml. An aqueous solution of 400 g of silver nitrate in 200 ml of water was flowed through the column filled with the diatomaceous earth. The column was allowed to stand for 30 minutes to carry the silver salt on the diatomaceous earth. Subsequently, hexane was flowed through the column to displace the column with hexane.

200 g of a raw material, an ethyl ester mixture of a highly unsaturated fatty acid having the composition shown in Table 5 were dissolved in 200 ml of hexane to prepare a hexane solution. This solution was flowed through the column. Initially, the column was developed by 2000 ml of hexane at a linear velocity of 0.5 to 5.0 cm/min, an eluate from the column was collected, and the solvent was removed under reduced pressure to concentrate the eluate, thus giving 114.5 g (yield 57.25%) of the first effluent fraction. Next, the column was developed by 2000 ml of a toluene mixed solvent containing 0.5% by volume of methanol at a linear velocity of 0.5 to 5.0 cm/min, an eluate from the column was collected, and the solvent was removed under reduced pressure to concentrate the eluate, thus giving 29.3 g (yield 14.65%) of the second effluent fraction.

Further, the column was developed by 2500 ml of a toluene mixed solvent containing 0.5% by volume of methanol at a linear velocity of 0.5 to 5.0 cm/min, an eluate from the column was collected, and the solvent was removed under reduced pressure to concentrate the eluate, thus giving 36.19 g (yield 18.10%) of the third effluent fraction. The resultant purified ethyl esters of fatty acids were analyzed by gas chromatography, with the following results shown in Table 5.

TABLE 5

| | Content of ethyl ester of each fatty acid (%) | | | | |
|---|---|---|---|---|---|
| | ETA (ω6) | ETA (ω3) | EPA | DHA | Others |
| Composition of raw material before purification | 0.04 | 0.23 | 20.42 | 63.39 | 15.92 |
| First effluent fraction | 0.08 | 0.41 | 29.03 | 42.97 | 27.51 |
| Second effluent fraction | 0.0 | 0.0 | 24.94 | 70.61 | 4.45 |
| Third effluent fraction | 0.0 | 0.0 | 0.61 | 99.38 | 0.01 |

As shown in Table 5, the present process exhibited high selectivity of DHA when the highly unsaturated fatty acid with high content of DHA was used as a raw material, and it could produce the fatty acid containing DHA in high purity of 99% or higher.

EXAMPLE 6

The separation and purification were carried out under the same conditions as in Example 1, but substituting the solvents shown in Table 6 for the toluene mixed solvent containing 0.5% by volume of methanol.

The purified ethyl esters of fatty acids obtained in the second effluent fraction were analyzed by gas chromatography, with the following results shown in Table 6.

TABLE 6

| | Yield of second effluent fraction (%) | Content of ethyl ester of each fatty acid (%) | | | | |
|---|---|---|---|---|---|---|
| | | ETA (ω6) | ETA (ω3) | EPA | DHA | Others |
| Composition of raw material before purification | | 3.65 | 2.07 | 45.02 | 8.73 | 40.53 |
| Developing solvents | | | | | | |
| 1. Toluene | 33.7 | 0.29 | 0.38 | 84.2 | 6.29 | 8.84 |
| 2. Toluene:ethyl acetate (2:1) | 22.2 | 0.33 | 0.03 | 94.5 | 0 | 5.14 |
| 3. Ethyl acetate | 29.1 | 1.21 | 1.05 | 81.0 | 1.61 | 15.13 |
| 4. Toluene:methanol (96:4) | 44.2 | 0.27 | 0.13 | 92.0 | 0.37 | 7.23 |
| 5. Toluene:methanol (96:2) | 38.1 | 0.68 | 0.66 | 80.0 | 5.75 | 12.91 |

The above result clearly shows that ETA (ω6, ω3) contained in the raw material before purification was largely reduced and also the composition of the effluent fatty acids varied depending on kinds of developing solvents because the polarity of the solvents was different. Most suitable solvent species and the combination thereof can be decided from the resultant composition and yield of the fatty acids or the like in accordance with the object.

Industrial applicability

The process for the separation and purification of highly unsaturated fatty acids or their derivatives according to the present invention is characterized by using as a carrier the diatomaceous earth having a large pore volume, preferably a pore size of 0.1–10 μm, a specific surface area of 0.5–50 m²/g, a pore volume of 1–10 ml/g and a bulk density of 0.1–0.3 g/ml, carrying a specified amount of silver (or silver salt) within the pore of the diatomaceous earth, forming a complex of the raw material to be treated, i.e., the mixture comprising the highly unsaturated acid or the esters thereof, with a silver ion, further using the silver-carried diatomaceous earth within the column, but not in a batch-wise manner, and flowing specified small amounts of solvents sequentially through the column, thereby selectively separating and purifying EPA and DHA or the esters thereof.

The present invention of the above construction can prepare the silver-carried diatomaceous earth easily, and can separate and purify EPA and DHA or the esters thereof in high purity. Further, the amount of the solvent used in the separation operation can be reduced, and the time required for separation can be reduced. This can provide a largely reduced running cost when the separation is performed on an industrial scale. Furthermore, the effusion of silver can be inhibited and the incorporation of silver into a separated and purified product can be prevented.

What is claimed is:

1. A process of selectively separating and purifying eicosapentaenoic and docosahexaenoic acids or the esters thereof from a mixture comprising a highly unsaturated fatty acid or the derivative thereof, which comprises the steps of:

flowing an aqueous medium comprising a silver salt through a column filled with a diatomaceous earth to carry the silver salt on the diatomaceous earth;

flowing a solvent solution of a mixture comprising the highly unsaturated fatty acid or the derivative thereof through the silver salt-carried diatomaceous earth in the column; and flowing a developing solvent through the column.

2. The process of claim 1 wherein the diatomaceous earth has a pore size of 0.1–10 $\mu$m, a specific surface area of 0.5–50 m$^2$/g and a pore volume of 1–10 ml/g.

3. The process of claim 1 wherein the silver salt carried is not more than 65% by weight in terms of silver, based on the weight of the diatomaceous earth.

4. The process of claim 1 wherein the developing solvent is pentane, hexane, heptane, toluene, xylene, methanol, isopropyl alcohol, ethyl acetate or the mixture thereof.

5. The process of claim 1 wherein the highly unsaturated fatty acid or the derivative thereof originates from a fish oil.

* * * * *

UNITED STATES PATENT AND TRADEMARK OFFICE
CERTIFICATE OF CORRECTION

PATENT NO.     : 6,313,330 B1
DATED          : November 6, 2001
INVENTOR(S)    : Kiyohara et al.

It is certified that error appears in the above-identified patent and that said Letters Patent is hereby corrected as shown below:

<u>Title page, Item [54] and Column 1, lines 1-5,</u>
The Title of Invention should read:
-- [54] PROCESSES OF SELECTIVELY SEPARATING AND PURIFYING EICOSAPENTAENOIC AND DOCOSAHEXAENOIC ACIDS OR THEIR ESTERS --

Signed and Sealed this

Second Day of July, 2002

*Attest:*

JAMES E. ROGAN
*Attesting Officer*   *Director of the United States Patent and Trademark Office*